United States Patent
Elleby et al.

(10) Patent No.: US 10,716,604 B2
(45) Date of Patent: Jul. 21, 2020

(54) BONE FUSING DEVICE FOR FUSING PHALANGES

(71) Applicants: Barron Douglas Elleby, Marietta, GA (US); Douglas Henry Elleby, Marietta, GA (US); Daniel Brian Lanois, Atlanta, GA (US)

(72) Inventors: Barron Douglas Elleby, Marietta, GA (US); Douglas Henry Elleby, Marietta, GA (US); Daniel Brian Lanois, Atlanta, GA (US)

(73) Assignee: Maurho Medical, Inc., Norwell, MA (US)

( * ) Notice: Subject to any disclaimer, the term of this patent is extended or adjusted under 35 U.S.C. 154(b) by 254 days.

(21) Appl. No.: 14/336,068

(22) Filed: Jul. 21, 2014

(65) Prior Publication Data
US 2016/0015437 A1    Jan. 21, 2016

(51) Int. Cl.
*A61B 17/72*      (2006.01)

(52) U.S. Cl.
CPC ...... *A61B 17/7291* (2013.01); *A61B 17/7283* (2013.01)

(58) Field of Classification Search
CPC .. A61F 2/4225; A61F 2/4241; A61B 17/7291; A61B 17/7208; A61B 17/7258; A61B 17/7283
USPC ......... 606/329; 623/21.11–21.19; 411/1–999
See application file for complete search history.

(56) References Cited

U.S. PATENT DOCUMENTS

| | | | | |
|---|---|---|---|---|
| 2,136,471 | A | * | 11/1938 | Schneider ............. A61B 17/72 411/458 |
| 3,737,128 | A | * | 6/1973 | Schuplin ............... F16B 19/004 248/71 |
| 5,053,035 | A | | 10/1991 | Mclaren |
| 5,368,261 | A | * | 11/1994 | Caveney ................ F16L 3/233 248/69 |
| 5,906,465 | A | * | 5/1999 | Sato ...................... F16B 21/084 248/68.1 |
| 6,458,134 | B1 | | 10/2002 | Songer et al. |
| 7,041,106 | B1 | * | 5/2006 | Carver ............... A61B 17/7291 606/309 |
| 8,100,983 | B2 | | 1/2012 | Schulte |
| 8,529,611 | B2 | | 9/2013 | Champagne et al. |
| 8,597,337 | B2 | | 12/2013 | Champagne |
| 8,715,325 | B2 | | 5/2014 | Weiner et al. |

(Continued)

FOREIGN PATENT DOCUMENTS

| DE | 19813914 | 9/1999 |
|---|---|---|
| GB | 2430625 | 4/2007 |

(Continued)

*Primary Examiner* — Matthew J Lawson
(74) *Attorney, Agent, or Firm* — David L. King

(57) ABSTRACT

A bone fusing device to connect and facilitate fusion between two adjacent phalanges in a body has a single elongated body having a first distal end and a second proximal end connected by a middle portion having four radially extending anti-rotation fins. Each end has a bone entry tip and a plurality of adjacent barbs. Each of the barbs has a sloped surface for entry into the bone and a sharp surface to prevent extraction once press fit into one of the phalanges. Preferably, the first distal end is shorter than the second proximal end. The elongated body is straight or has affixed bend at a location in the middle portion.

12 Claims, 5 Drawing Sheets

(56) References Cited

U.S. PATENT DOCUMENTS

| | | | |
|---|---|---|---|
| 2007/0282342 A1 | 12/2007 | Niederberger et al. | |
| 2008/0138169 A1* | 6/2008 | Jackson | F16B 5/0642 411/450 |
| 2009/0324360 A1* | 12/2009 | Schuech | F16B 21/082 411/33 |
| 2011/0082508 A1 | 4/2011 | Reed | |
| 2011/0125153 A1* | 5/2011 | Tyber | A61B 17/1717 606/62 |
| 2012/0065692 A1* | 3/2012 | Champagne | A61B 17/7291 606/311 |
| 2013/0053975 A1 | 2/2013 | Reed et al. | |
| 2013/0066435 A1* | 3/2013 | Averous | A61F 2/42 623/21.11 |
| 2014/0025124 A1* | 1/2014 | Champagne | A61B 17/863 606/308 |
| 2014/0188237 A1* | 7/2014 | McCormick | A61F 5/019 623/21.19 |
| 2014/0277554 A1* | 9/2014 | Roman | A61F 2/4225 623/21.19 |
| 2014/0309747 A1* | 10/2014 | Taylor | A61F 2/42 623/21.11 |
| 2015/0219136 A1* | 8/2015 | Koelling | F16B 19/002 411/510 |
| 2015/0219137 A1* | 8/2015 | Koelling | F16B 19/002 29/453 |

FOREIGN PATENT DOCUMENTS

| | | |
|---|---|---|
| WO | 2013131974 | 9/2013 |
| WO | 2013177252 | 11/2013 |

\* cited by examiner

BONE FUSING DEVICE FOR FUSING PHALANGES

TECHNICAL FIELD

The present invention relates to devices for insertion into adjacent bone segments, more particularly to a device for insertion into two adjacent phalanges in a body.

BACKGROUND OF THE INVENTION

The occurrence of issues with the joints and bones of the feet and hands are well documented. In the foot, conditions of bone misalignment at the joints is very common, one of the most common is called a hammertoe. A hammer toe is a very common foot problem that can affect one or more toes. A hammer toe has a characteristic appearance as being elevated at the middle part of the toe, while the end of the toe flexes downward. While most hammer toes occur on adult feet, they can sometimes affect children as well.

The lesser toes, rather than the big toe, are where most often one sees hammer toes occur. Each of these toes typically has three bones (phalanges) and three joints. A hammer toe occurs when there is a flexion (downward) contracture of the proximal interphalangeal joint (PIPJ) and an extension (upward) contracture of the metatarsophalangeal joint (MTPJ).

A hammer toe is a toe that stays in a curled or flexed position. It can be caused by a muscle imbalance, arthritis, or shoes that do not fit well. Hammer toe can occur in more than one toe.

Several different kinds of surgery can repair hammer toe. A bone or foot doctor will recommend the kind that will work best. Some of the surgeries include: remove parts of the toe bones; cut or transplant the tendons of the toes (tendons connect bone to muscle); and fuse the joint together to make the toe straight and no longer able to bend. After surgery, surgical pins or a wire (Kirschner, or K-wire) can be used to hold the toe bones in place while the toe heals.

A number of devices or bone fusing devices have been developed to help hold the joint to be fused. These devices often employ a bendable or flexible joint and are configured in two or more pieces connected at the bendable joint. These devices are complex to make and difficult to hold in position.

The present invention provides a unique improvement in the fusion devices for this type of misalignment.

SUMMARY OF THE INVENTION

A bone fusing device to connect and facilitate fusion between two adjacent phalanges in a body has a single elongated body having a first distal end and a second proximal end connected by a middle portion having four radially extending anti-rotation fins. Each end has a bone entry tip and a plurality of adjacent barbs. Each of the barbs has a sloped surface for entry into the bone and a sharp surface to prevent extraction once press fit into one of the phalanges. Preferably, the first distal end is shorter than the second proximal end. The elongated body is straight or has an affixed bend at a location in the middle portion. The bend forms a drop angle θ of 5 degrees to 15 degrees relative first and second ends; most preferably the drop angle θ is 10 degrees.

The two or more anti-rotation fins are equally spaced about the body. Preferably there are four fins oriented at 0 degrees, 90 degrees, 180 degrees and 270 degrees relative to the cross section of the elongated body. The fins have a first tapered end extending and starting from a last barb at the first distal end. Each fin extends through the middle portion or past the bend location toward the second proximal end and has a tapered second end. The tapered second end of the fins terminates on the middle portion spaced from a last barb of the second proximal end. The bend angle θ aligns with the top or 0 degree fin and bottom or 180 degree fin. The top fin has a convexity at a maximum height and the bottom has a concavity at the maximum height. The maximum height straddles and extends about the bend. The bone fusing device can made of an implantable metal such as titanium or stainless steel. Alternatively, the device can be an implantable plastic, such as PEEK or can be a plastic that is slightly flexible such as nylon or polyethylene. The device can also be a biocomposite or bioresorbable polymer.

BRIEF DESCRIPTION OF THE DRAWINGS

The invention will be described by way of example and with reference to the accompanying drawings in which.

DETAILED DESCRIPTION OF THE INVENTION

Figure 1:
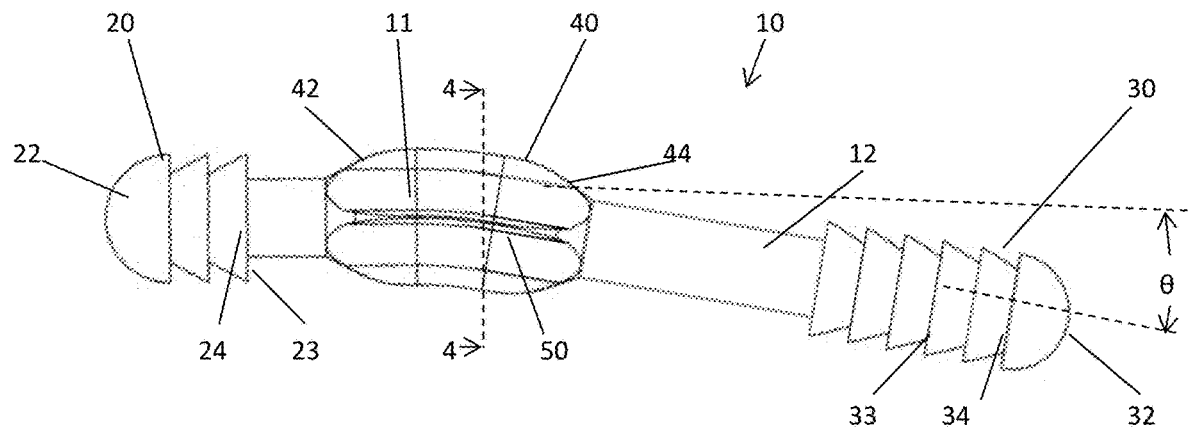
FIG. 1 is a side plan view of a first embodiment of the bone anchor device of the present invention.

With reference to the drawings, FIGS. 1-4B show the bone anchor device 10 of the present invention. The device 10, as illustrated, has a single piece angled elongated body 11 having a first distal end 20 and a second proximal end 30 connected by a middle portion 12 having four radially extending anti-rotation fins 40. The device 10 is configured to facilitate bone fusion between adjacent bone phalanges in a body.

Each end 20, 30 has a tip 22, 32 respectively. Adjacent the tips 22, 32 are barbs 24, 34 respectively. As illustrated, the bone entry tips 22, 32 are rounded, generally hemispherical in shape having a sharp edged surface 23, 33 adjacent the barbs 24, 34. Each barb 24, 34 has a similar sloped entry surface which can be conical or semi-spherical for easy bone entry and a sharp edge surface 23, 33 respectively to prevent or resist extraction once the device 10 is press fit into the phalange.

As illustrated, the distal end 20 is shorter in length than the second proximal end 30 and at a location in the middle portion 12 of the elongated body 11 is a bend 50 exhibiting an angle θ, θ being a drop angle between 5 degrees and 15 degrees relative to the respective ends 20, 30 preferably between 8 degrees and 12 degrees, ideally 10 degrees.

As shown in FIG. 1, a straight line extending from the distal end 20 shows the inclination θ. This fixed angle closely duplicates the natural bend of the adjacent distal and middle phalanges.

Figure 4:
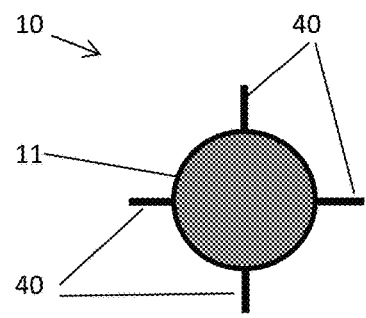
FIG. 4 is a cross sectional view taken along line 4-4 of FIG. 1.

With reference to the anti-rotation fins 40, as shown in FIG. 4, the four fins 40 are oriented at 90 degree intervals with one fin 40 on the top, one fin 40 on the bottom and two fins 40 extending from opposite sides or using the 360 degree analogy; at the 0 degree, 90 degree, 180 degree and 270 degree locations. These fins 40 start at a location adjacent a last entry barb 24 of the distal end 20 and extend through the bend 50 toward the proximal end 30, but terminating on a smooth diameter or surface of the middle portion 12. The fins 40 have tapered ends 42, 44 that extend to a maximum height along the bend 50. In FIG. 1 as shown in the top fin 40, at the maximum height exhibits a path parallel to the middle portion of the elongated body 11 having a convex bend whereas the lower fin 40 has a parallel form with a slight concavity to mimic the bend 50 and the path of the middle portion 12.

Figure 2:
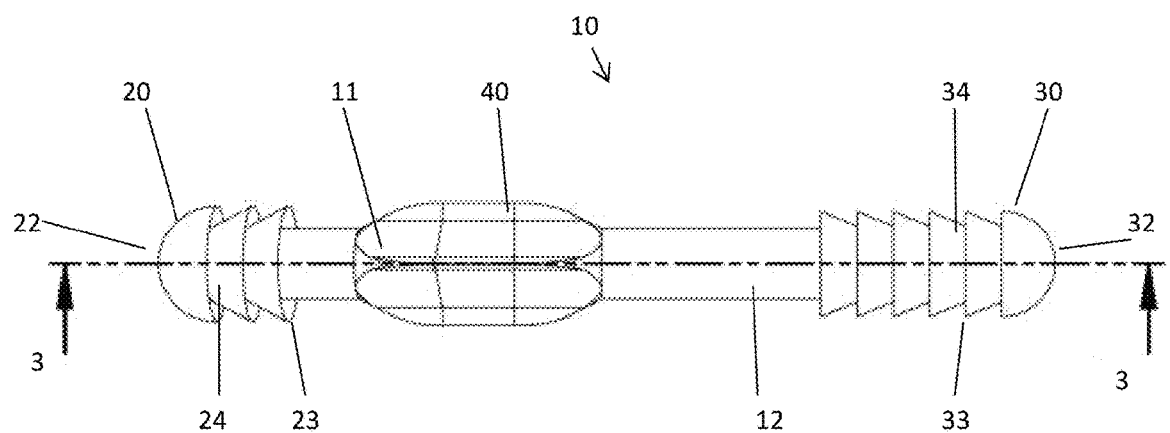
FIG. 2 is a top plan view of the first embodiment device of FIG. 1.
Figure 3:
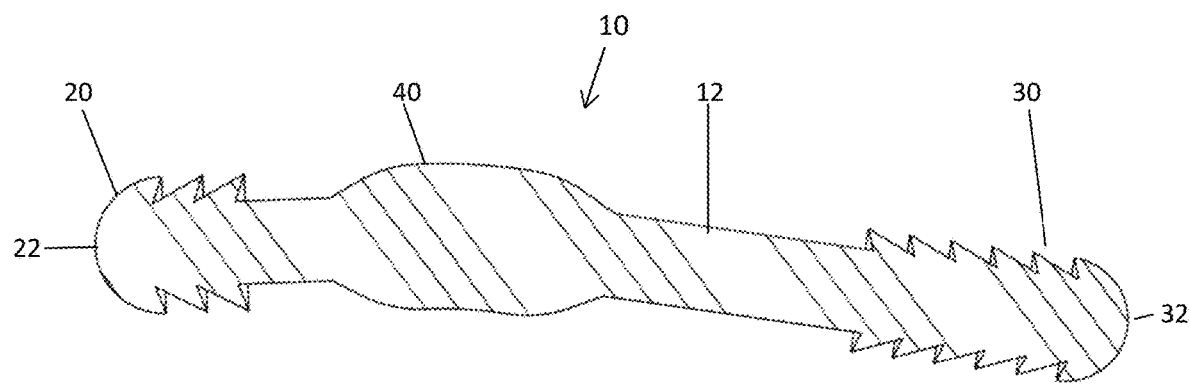
FIG. 3 is a cross sectional view of the first embodiment device taken along lines 3-3 of FIG. 2.
Figure 4A:
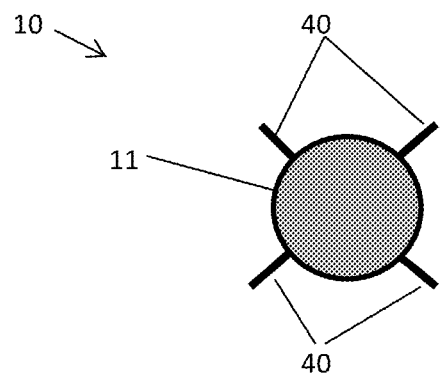
FIG. 4A is a cross sectional view of an "X" fin configuration taken along line 4-4 of FIG. 1.
Figure 4B:
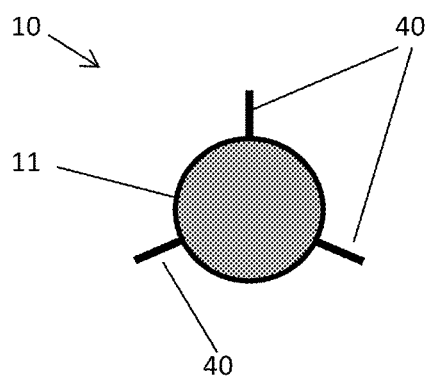
FIG. 4B is a cross sectional view of a three fin configuration taken along line 4-4 of FIG. 1.
Figure 5:
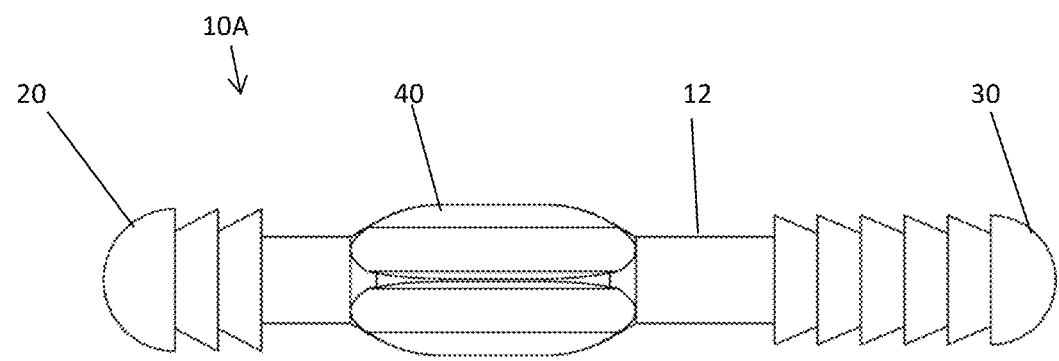
FIG. 5 is a side plan view of a second embodiment of the bone anchor device of the present invention.
Figure 6:
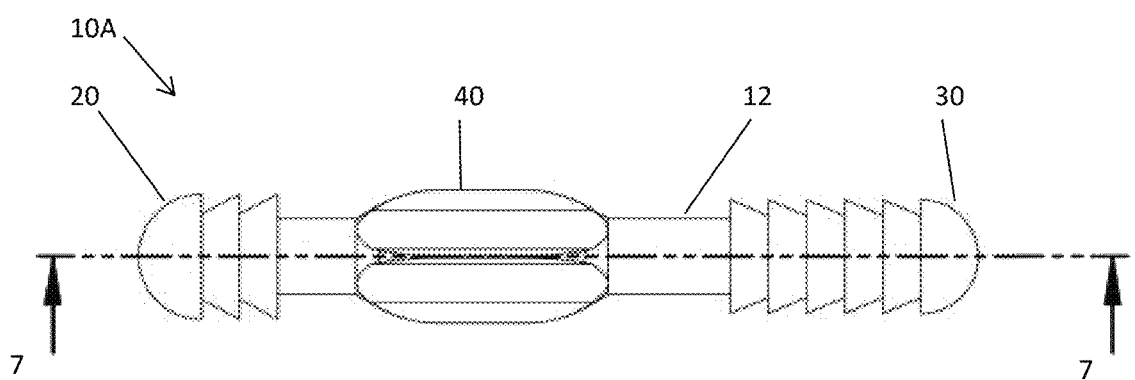
FIG. 6 is a top plan view of the second embodiment device of FIG. 5.
Figure 7:
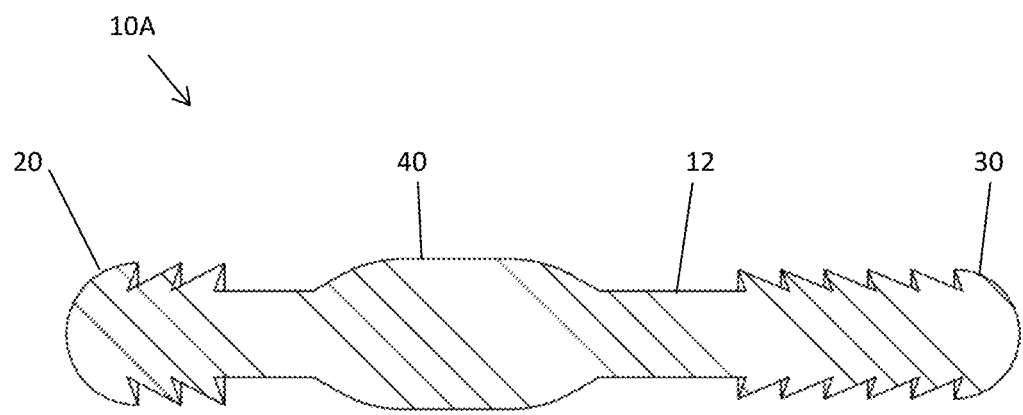
FIG. 7 is a cross sectional view taken along lines 7-7 of FIG. 5.
Figure 8A:
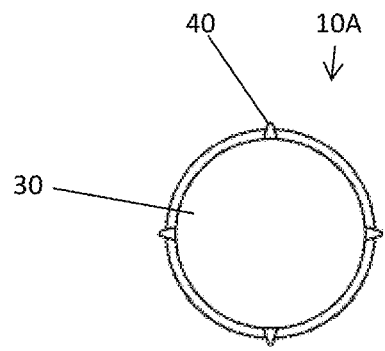
FIG. 8A is a proximal end view of the second embodiment device of FIG. 5.
Figure 8B:
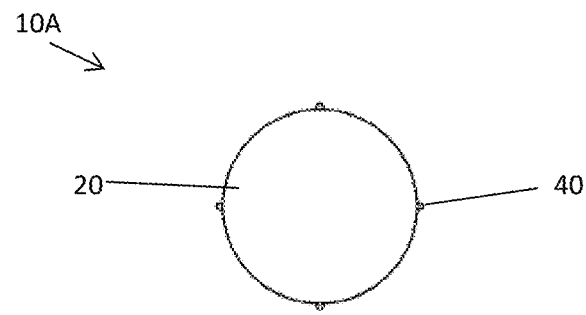
FIG. 8B is a distal end view of the second embodiment device of FIG. 5.

As shown in FIG. 2, the top view illustrates the side fins 40 are generally straight along the maximum height and show no curvature. The fins 40 are relatively thin in thickness, but sufficiently thick to resist torsion bending when the device is installed. As shown in FIG. 4A, the use of four fins could be alternatively oriented at 90 degrees along the 45 degrees, 135 degrees, 225 degrees and 315 degrees to form an "X" top configuration as opposed to the illustrated "+". Optionally, as shown in FIG. 4B, only three fins 40 could have been used spaced 120 degrees apart at 0 degrees, 120 degrees and 240 degrees to achieve the anti-rotation. However, the "+" orientation provides an absolute line of sight correct aligned vertical feature to insure the bend 50 is properly oriented as the device is implanted. This is critical because the configuration of the tip 22, 32 and barbs 24, 34 are not designed to allow multiple insertions into a prepared pre-drilled hole in a phalange. Accordingly, the design as configured allows the surgeon to make an exactly correct orientation of the device 10 every time.

As shown in FIGS. 5-8, a second embodiment device 10A is shown with the elongated body 11 being straight with a zero degree bend angle.

The device 10, 10A is an ideal hammertoe fixation device designed to fuse the distal phalangeal bone with the middle phalanx or middle phalangeal bone. The purpose for the device 10 is to correct a degenerated joint between the distal and middle phalanx. The procedure includes a superior incision on the toe lengthwise opening up the joint capsule, removing a small portion of each bone, the distal phalanx and the middle phalanx, and preparing a pilot hole, a drill is used to create a pilot hole to a desired depth based on the size of the patient and the size of the device 10 going in. The surgeon would broach the fin feature 40 into the two ends of the bone that were prepared with the pilot hole and then he would insert the shorter distal end 20 into the distal phalanx, pull the joint apart and insert the proximal end 30 with the tip 32 and barbs 34 into the middle phalanx. At that point, he would take and compress the two bones together over the bone fusing device 10 making sure to align the four fins 40 most particularly the top fin 40 to broach with the anti-rotation fins 40 of the implanted bone fusing device penetrating the interior cancellous bone. The device 10, when installed, prevents rotation post-op and will give a longer better lasting outcome for the patient as, once installed, the device 10 cannot rotate or become misaligned at the bend 50.

As shown, the device 10, 10A can be provided in a wide range of sizes. The exemplary device 10 had a first distal end length of 9 mm and second proximal end length of 16 mm and the ends 20, 30 have differing diameters of a first distal end 20 diameter of 3.3 mm and a second proximal end 30 diameter of 3.0 mm at the tips 22, 32 and the barbs 24, 34. These end diameters could be equal to allow the surgeon to use one drill size for each phalange as a matter of convenience. The device 10 had fins of total equal height and width of 3.5 mm. These fins exhibiting a greater size than either the distal end or proximal end ensures the fins adequate purchase into uncompromised boney surfaces. The importance of the fin(s) purchase into uncompromised boney tissue should not be understated as this is the design intent and inadequate purchase would yield insufficient anti-rotation characteristics. As shown, the device 10 is preferably made of an implantable grade stainless steel. The device 10 could also be made of a suitable polymer or implantable plastic, such plastic is PEEK. However, if some minor flexing is desirable at the bend 50, a suitable material like polyethylene or nylon could be used. The device 10 could also be machined or cast metal such as titanium. Finally, the device 10 could also be made of a suitable bio-composite or bio-resorbable polymer material to provide structure during healing with eventual resorption upon successful joint fusion.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone fusing device to connect and facilitate fusion between two adjacent phalanges in a body; comprising:
    a single elongated body having a first distal end and a second proximal end connected by a middle portion having four radially extending anti-rotation fins, the first distal end being shorter than the second proximal end and the elongated body having an affixed bend at a location in the middle portion, wherein the four anti-rotation fins are oriented at 0 degrees, 90 degrees, 180 degrees and 270 degrees relative to a cross section of the middle portion of the elongated body; and
    wherein each end has a rounded generally hemispherical in shape bone entry tip and a plurality of adjacent barbs, the first distal end having a length of 9 mm and a diameter of 3.3 mm or equal to the diameter of the second proximal end, the second proximal end having a length of 16 mm and a diameter of 3.0 mm, each of the barbs has a sloped surface which is semi-spherical for entry into the bone and a sharp surface configured to allow rotation and to prevent extraction once press fit into one of the phalanges, the fins have a first end extending and starting spaced a distance from a last barb at the first distal end, each fin extending past the affixed bend toward the second proximal end to a tapered second end on the middle portion spaced a distance from a last barb at the second proximal end, the fins having a total height of 3.5 mm exhibiting a greater size than the diameters of the first distal and second proximal ends, the fins being configured to engage uncompromised boney tissue to prevent rotation, wherein the bend forms a drop angle θ of 5 degrees to 15 degrees relative first and second ends and the drop angle θ aligns with the top or 0 degree and bottom or 180 degree fins, the top fin having a convexity at a maximum height and the bottom having a concavity at the maximum height, the maximum height straddling and extending about the bend wherein the first distal end and the second proximal end are semi-spherical shaped with the anti-rotation fins disposed in the middle portion spanning the bend providing the anti-rotation feature, wherein upon insertion of the device a surgeon would insert the distal end of the device into a distal phalanx bone and pull the joint apart and insert the proximal end of the device into a middle phalanx bone and rotatingly align the two bones and compress the bones together with the 0 degree fin on top as the anti-rotation fins broach the two bones to prevent post op rotation or misalignment.

2. The bone fusing device of claim 1 wherein the bone fusing device is made of an implantable plastic.

3. The bone fusing device of claim 2 wherein the plastic being PEEK.

4. The bone fusing device of claim 2 wherein the plastic being a slightly flexible nylon or polyethylene.

5. The bone fusing device of claim 1 wherein the device is metal.

6. The bone fusing device of claim 5 wherein the device is titanium or stainless steel.

7. A bone fusing device to connect and facilitate fusion between two adjacent phalanges in a body; comprising:
   a single elongated body having a first distal end and a second proximal end connected by a middle portion having four radially extending anti-rotation fins, the first distal end being shorter than the second proximal end and the elongated body having an affixed bend at a location in the middle portion, wherein the four anti-rotation fins are oriented at 0 degrees, 90 degrees, 180 degrees and 270 degrees relative to a cross section of the middle portion of the elongated body; and
   wherein each end has a rounded generally hemispherical in shape bone entry tip and a plurality of adjacent barbs, the first distal end having a length of 9 mm and a diameter of 3.3 mm or equal to the diameter of the second proximal end, the second proximal end having a length of 16 mm and a diameter of 3.0 mm, each of the barbs has a sloped surface which is semi-spherical for entry into the bone and a sharp surface configured to allow rotation and to prevent extraction once press fit into one of the phalanges, the fins have a first end extending and starting spaced a distance from a last barb at the first distal end, each fin extending past the affixed bend toward the second proximal end to a tapered second end on the middle portion spaced a distance from a last barb at the second proximal end, the fins having a total height of 3.5 mm exhibiting a greater size than the diameters of the first distal and second proximal ends, the fins being configured to engage uncompromised boney tissue to prevent rotation, wherein the bend forms a drop angle θ of 10 degrees relative first and second ends and the drop angle θ aligns with the top or 0 degree and bottom or 180 degree fins, the top fin having a convexity at a maximum height and the bottom having a concavity at the maximum height, the maximum height straddling and extending about the bend wherein the first distal end and the second proximal end are semi-spherical shaped with the anti-rotation fins disposed in the middle portion spanning the bend providing the anti-rotation feature, and wherein upon insertion of the device a surgeon would insert the distal end of the device into a distal phalanx bone and pull the joint apart and insert the proximal end of the device into a middle phalanx bone and rotatingly align the two bones and compress the bones together with the 0 degree fin on top as the anti-rotation fins broach the two bones to prevent post op rotation or misalignment.

8. The bone fusing device of claim 7 wherein the bone fusing device is made of an implantable plastic.

9. The bone fusing device of claim 8 wherein the plastic being PEEK.

10. The bone fusing device of claim 8 wherein the plastic being a slightly flexible nylon or polyethylene.

11. The bone fusing device of claim 7 wherein the device is metal.

12. The bone fusing device of claim 11 wherein the device is titanium or stainless steel.

* * * * *